United States Patent [19]

Kanne

[11] Patent Number: 5,189,169
[45] Date of Patent: Feb. 23, 1993

[54] PHOSPHORODIAMIDOTHIOATE HERBICIDES

[75] Inventor: David B. Kanne, Corte Madera, Calif.

[73] Assignee: Imperial Chemical Industries PLC, London, Great Britain

[21] Appl. No.: 790,788

[22] Filed: Nov. 12, 1991

[51] Int. Cl.$^5$ .............................. C07F 9/58; C07F 9/24
[52] U.S. Cl. ........................................ 546/22; 546/21; 558/195; 558/199; 558/200
[58] Field of Search ...................... 546/21, 22; 558/195, 558/199, 200, 81

[56] References Cited

U.S. PATENT DOCUMENTS

| | | | |
|---|---|---|---|
| 2,502,966 | 4/1950 | Kosolapoff | 562/878 |
| 2,765,252 | 10/1956 | Pianka et al. | 514/138 |
| 2,814,636 | 11/1957 | Stahmann et al. | 514/106 |
| 2,912,541 | 11/1959 | Godfrey | 335/154 |
| 2,957,018 | 10/1960 | Baker | 558/167 |
| 2,993,775 | 7/1961 | Baker | 71/71 |
| 2,993,776 | 7/1961 | Chupp | 71/86 |
| 3,089,808 | 5/1963 | Meltzer et al. | 558/200 X |
| 3,433,623 | 3/1969 | Bayer et al. | 71/86 |
| 3,454,682 | 7/1969 | Haynes et al. | 558/199 |
| 3,504,086 | 3/1970 | Aichenegg | 514/134 |
| 3,531,550 | 9/1970 | Herber et al. | 558/200 |
| 3,539,331 | 11/1970 | Smith | 71/71 |
| 3,983,188 | 9/1976 | Walsh | 558/192 |
| 4,315,870 | 2/1982 | Ollinger | 558/178 |
| 4,387,060 | 6/1989 | Hoffmann et al. | 558/81 |

FOREIGN PATENT DOCUMENTS

| | | |
|---|---|---|
| 137478 | 12/1969 | Czechoslovakia . |
| 963876 | 5/1957 | Fed. Rep. of Germany . |
| 115568 | 10/1975 | German Democratic Rep. . |
| 43-4340 | 2/1968 | Japan . |
| 60-42390 | 3/1985 | Japan . |
| 6700910 | 7/1967 | Netherlands . |
| 491647 | 11/1976 | U.S.S.R. . |
| 1350286 | 4/1974 | United Kingdom . |

OTHER PUBLICATIONS

Blindheim, et al., Spectochimica Acta, 25A.
Cheymol, et al., C. R. Hebd. Seances Acad. Sci. 249, 1240 (1959).
Friedman, et al., J. Med. Chem. 6, 92 (1962).
Kabachnik, et al., Zh. Obshch. Khim., 35, 1476 (1965).
Liu, Chem. Abstr. 110: 149755x (1989).
Martin, et al., C. R. Hebd. Seances Acad. Sci. 225, 2095 (1962).
Nifant'ev, et al., Zh. Obshch. Khim., 43, 2658 (1973).
Sturtz, et al., Synthesis, 730 (1974).
Westheimer, et al., Acc. Chem. Res., 1, 70 (1968).

Primary Examiner—Mary Lee
Assistant Examiner—Michael G. Ambrose
Attorney, Agent, or Firm—Joel G. Ackerman

[57] ABSTRACT

Herbicides having the formula

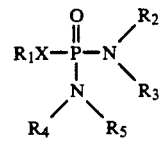

in which X is oxygen or sulfur; and if X is sulfur, $R_1$ is $C_1$–$C_6$ alkyl, $C_5$–$C_6$ cycloalkyl, allyl, phenyl, tolyl, chlorophenyl, 3,4-dichlorophenyl, or phen-($C_1$–$C_2$)alkyl; $R_2$ is $C_1$–$C_4$ alkyl, $C_2$–$C_4$ alkoxyalkyl, or allyl; $R_3$ is $C_1$–$C_4$ alkyl, $C_1$–$C_4$ alkoxyalkyl, pyridyl, phenyl or substituted phenyl in which the substituents are halogen, $C_1$–$C_4$ alkyl, $C_1$–$C_4$ alkoxy, $C_1$–$C_4$ haloalkoxy, nitro and/or cyano; or $R_2$ and $R_3$ taken together form an alkylene chain having from 2 to 6 carbon atoms optionally substituted by up to two $C_1$–$C_4$ alkyl groups; if $R_3$ is alkyl or alkoxyalkyl, then $R_4$ and $R_5$ are each $C_2$–$C_4$ alkyl; if $R_3$ is phenyl, substituted phenyl or pyridyl, then $R_4$ and $R_5$ are $C_2$–$C_6$ alkyl, phenyl or substituted phenyl; or $R_3$ and $R_5$ taken together form an alkylene chain having from 2 to 5 carbon atoms and $R_4$ is $C_2$–$C_4$ alkyl;

and if X is oxygen, $R_1$ and $R_4$ taken together form an alkylene ring having from 2 to 5 carbon atoms and $R_2$, $R_3$ and $R_5$ are each $C_2$–$C_4$ alkyl; provided that $R_3$ is not 2,3,6-trifluorophenyl are described.

22 Claims, No Drawings

PHOSPHORODIAMIDOTHIOATE HERBICIDES

BACKGROUND AND PRIOR ART

This invention relates to the use of certain phosphorodiamidate compounds as herbicides.

Dutch patent application 67.00910 discloses a series of nematocidal phosphoro mono- and diamidothioates. Russian patent 491,647 discloses a process for preparation of phosphorodiamidothioates which are said to possess various types of biological activity.

DESCRIPTION OF THE INVENTION

In one aspect, this invention relates to the use as herbicides of compounds having the formula

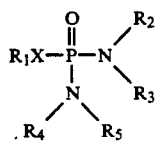

in which X is oxygen or sulfur; and if X is sulfur, $R_1$ is $C_1$–$C_6$ alkyl, $C_5$–$C_6$ cycloalkyl, allyl, phenyl, tolyl, chlorophenyl, 3,4-dichlorophenyl, or phen-($C_1$–$C_2$)alkyl; $R_2$ is $C_1$–$C_4$ alkyl, $C_2$–$C_4$ alkoxyalkyl, or allyl; $R_3$ is $C_1$–$C_4$ alkyl, $C_1$–$C_4$ alkoxyalkyl, pyridyl, phenyl or substituted phenyl in which the substituents are halogen, $C_1$–$C_4$ alkyl, $C_1$–$C_4$ alkoxy $C_1$–$C_4$ haloalkoxy, nitro and/or cyano; or $R_2$ and $R_3$ taken together form an alkylene chain having from 2 to 6 carbon atoms optionally substituted by up to two $C_1$–$C_4$ alkyl groups; if $R_3$ is alkyl or alkoxyalkyl, then $R_4$ and $R_5$ are each $C_2$–$C_4$ alkyl; if $R_3$ is phenyl, substituted phenyl or pyridyl, then $R_4$ and $R_5$ are $C_2$–$C_6$ alkyl, phenyl or substituted phenyl; or $R_3$ and $R_5$ taken together form an alkylene chain having from 2 to 5 carbon atoms and $T_4$ is $C_2$–$C_4$ alkyl;

and if X is oxygen, $R_1$ and $R_4$ taken together form an alkylene ring having from 2 to 5 carbon atoms and $R_2$, $R_3$ and $R_5$ are each $C_2$–$C_4$ alkyl; provided that $R_3$ is not 2,4,6-trifluorophenyl.

Some compounds of the class just described have been described in the Dutch patent application and Russian patent mentioned above, and in literature dealing with research in organic chemistry and/or spectroscopy. Others, however, are novel and form another aspect of this invention, namely compounds which have the formula

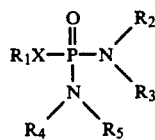

in which X is sulfur or oxygen; and if X is sulfur, $R_1$ is $C_1$–$C_6$ alkyl, phenyl, tolyl, chlorophenyl or 3,4-dichlorophenyl; $R_2$ is $C_1$–$C_4$ alkyl; $R_3$ is pyridyl, phenyl or substituted phenyl in which the substituents are halogen, $C_1$–$C_4$ alkyl, $C_1$–$C_4$ alkoxy, $C_1$–$C_4$ haloalkoxy, nitro and/or cyano; or $R_2$ and $R_3$ taken together form an alkylene chain having from 2 to 6 carbon atoms optionally substituted by up to two $C_1$–$C_4$ alkyl groups; $R_4$ and $R_5$ are each $C_2$–$C_6$ alkyl; or $R_3$ and $R_5$ taken together form an alkylene chain having from 2 to 5 carbon atoms;

and if X is oxygen, $R_1$ and $R_4$ taken together form an alkylene chain having from 2 to 5 carbon atoms and $R_2$, $R_3$ and $R_5$ are each $C_2$–$C_4$ alkyl; provided that $R_3$ is not 2,3,6-trifluorophenyl.

The term "alkyl" includes straight and branched chained acyclic hydrocarbyl moieties having the indicated number of carbon atoms. Preferred alkyl groups include methyl, ethyl, n-propyl, isopropyl, n-butyl, s-butyl, t-butyl, and n-hexyl. A preferred cycloalkyl group is cyclohexyl. Preferred alkoxy and haloalkoxy groups are methoxy, ethoxy and trifluoromethoxy. The term "halogen" includes chloro, bromo, fluoro and iodo. Substituted phenyl groups may contain one or more of the indicated substituents, which may be the same or different. Preferably, the substituted phenyl groups contain from one to three substituents, which may be located at convenient points on the phenyl ring.

As used herein, the term "herbicide" means a compound or composition which adversely controls or modifies the growth of plants. By the term "herbicidally effective amount" is meant any amount of such compound or composition which causes an adverse modifying effect upon the growth of plants. By "plants", it is meant germinant seeds, emerging seedlings and established vegetation, including roots and above-ground portions. Such controlling or modifying effects include all deviations from natural development, such as killing, retardation, defoliation, desiccation, regulation, stunting, tillering, leaf burn, dwarfing, and the like.

The compounds of this invention have been found to be active herbicides, particularly post-emergent herbicides; i.e. they may be applied to control or kill existing vegetation which has already emerged from the soil. Some of the compounds of this invention have demonstrated such post-emergence herbicidal activity in a relatively short time, and against some weeds, with a very strong effect. Herbicides having such rapid and extensive post-emergence activity are sometimes referred to as "contact and burn" or "burn-down" herbicides and are used, among other applications, for clearing vegetation from land such as building lots, highway median strips, railroad tract beds, and crop land prior to planting or in minimum till or no-till farming. Some of the compounds of this invention also demonstrate pre-emergence activity, that is, control or killing of vegetation by application prior to the emergence of vegetation from the soil. Pre-emergence herbicides may be applied by techniques such as incorporation into, or spraying or spreading onto, the surface of the soil. Compounds showing "contact-and-burn" effect, but little or no pre-emergence activity, may be useful in clearing land prior to planting since planting of a crop can be done relatively soon after the herbicide is applied.

Compounds showing "contact-and-burn" effect, but little or no pre-emergence activity, may be useful in clearing land prior to planting since planting of a crop can be done relatively soon after the herbicide is applied.

The compounds of this invention in which X is sulfur may be prepared according to any of several processes known in the art for preparing phosphoroamidate compounds in general. For instance, depending on the substituents, they may be prepared from starting phosphorodichlorides and an appropriate amine, or amines, by the general reaction

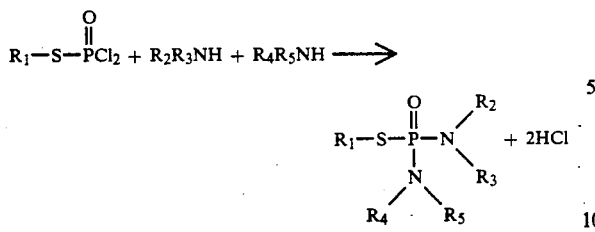

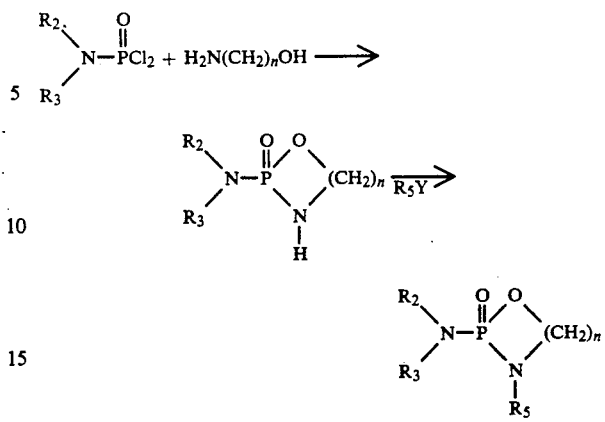

Processes of this type in general are carried out at temperatures of from about 0° to about 25° C., preferably from about 0° to about 10° C., in the presence of an inert solvent such as toluene, and a base. The hydrogen chloride produced during the reaction forms a salt, for instance an amine hydrochloride, which is removed conventionally from the reaction products.

Another process which may be used to prepare compounds for this invention involves reaction of an appropriate mercaptide with a diamino substituted phosphoryl chloride according to the reaction

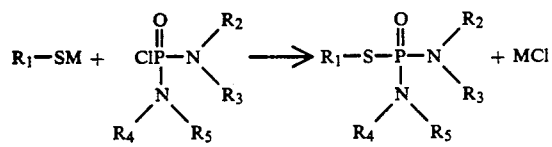

in which M is an alkali metal, preferably sodium or potassium. Such processes are generally carried out as known in the art at temperatures of from about 0° to about 60° C., preferably from about 25° to about 40° C. in the presence of an inert solvent such as tetrahydrofuran.

Starting materials

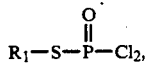

if not readily available, may be prepared from the corresponding mercaptan and phosphorus trichloride according to the reaction:

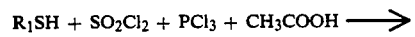

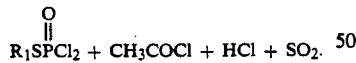

The starting materials

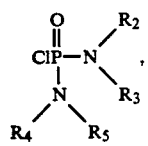

if not readily available, may be prepared by addition of two equivalents of the appropriate amine to phosphorus oxychloride in a solvent such as methylene chloride at temperatures of about 0°-25° C.

The cyclic compounds of this invention in which X is oxygen may be prepared in two steps by cyclization of a dialkylaminophosphorodichloride with an alkanolamine, followed by alkylation:

in which n is an integer of from 2 to 5 and Y is a halogen.

The cyclization step is conducted at temperatures of from about 0° to about 25° C., in an inert solvent such as tetrahydrofuran or a chlorinated solvent such as methylene chloride, in the presence of two equivalents of above, preferably a tertiary amine.

The alkylation step is conducted at similar temperatures, using similar solvents in the presence of an alkali metal hydride.

The following represent examples of preparation of compounds of this invention.

EXAMPLE 1

Preparation of S-n-propyl-tetra(n-butyl) phosphorodiamide (Compound No. 7 herein)

In a flask, 0.34 g (4.4 mmol) of n-propylmercaptan was reacted with 4.4 mmol oil-free sodium hydride, in 1.5 ml tetrahydrofuran to produce sodium n-propylmercaptide. To this was added 1.5 g (4.4 mmol) tetrabutylphosphorodiamidic chloride, at room temperature. The reaction was heated and additional mercaptide added until all this diamidic chloride had reacted. Then the reaction mixture was cooled, and 50 ml cold water and 50 ml ether were added. The aqueous phase was extracted with ether; the organic phases were combined, dried and solvent evaporated to yield 1.77 g of product, identified by spectroscopy.

EXAMPLE 2

Preparation of 1-(N,N-dipropylamino)-2-aza-5-oxa-1-phosphacyclohexane (Compound 146 herein)

Cyclization

In a flask were placed 3.0 g (13.8 mmol) di-n-propylaminophosphoryl chloride, 4.2 mL (30 mmol) triethylamine and 20 ml dichloromethane, at room temperature. Then, there was added dropwise a solution of 1.03 g (13.8 mmol) 3-amino-1-propanol in 5 mL dichloromethane. The mixture was stirred for 14 hours. Triethylamine hydrochloride was removed by filtration. The filtrate was washed with water and with saturated sodium chloride, dried and evaporated, yielding a clear orange oil.

Alkylation

To a slurry of 0.7 g (4.5 mmol) oil-free potassium hydride in 6 mL tetrahydrofuran (at room temperature under a nitrogen blanket) was slowly added a solution of 1.0 g (4.5 mmol) of the cyclic product of the previous step in 4 mL tetrahydrofuran. The mixture was stirred for 4 hours; then it was diluted with 60 mL ether, washed, dried and evaporated to produce 1.01 g of a clear colorless mobile oil, identified spectroscopically as the desired product.

Table I depicts representative compounds of this invention, prepared by one of the processes described above. Structures were confirmed by spectroscopic analyses.

TABLE I

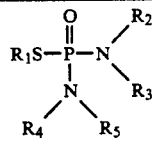

| Compound No. | $R_1$ | $R_2$ | $R_3$ | $R_4$ | $R_5$ | m.p. °C. or $n_D^{30}$ |
|---|---|---|---|---|---|---|
| 1. | n-$C_4H_9$ | n-$C_3H_7$ | n-$C_3H_7$ | n-$C_3H_7$ | n-$C_3H_7$ | oil |
| 2. | n-$C_3H_7$ | $CH_3$ | $C_2H_5$ | n-$C_3H_7$ | n-$C_3H_7$ | oil |
| 3. | t-$C_4H_9$ | n-$C_3H_7$ | n-$C_3H_7$ | n-$C_3H_7$ | n-$C_3H_7$ | oil |
| 4. | n-$C_5H_{11}$ | n-$C_4H_9$ | n-$C_4H_9$ | n-$C_4H_9$ | n-$C_4H_9$ | oil |
| 5. | 2-$CH_3C_6H_4$ | n-$C_3H_7$ | n-$C_3H_7$ | n-$C_3H_7$ | n-$C_3H_7$ | oil |
| 6. | 4-$ClC_6H_4$ | n-$C_3H_7$ | n-$C_3H_7$ | n-$C_3H_7$ | n-$C_3H_7$ | oil |
| 7. | n-$C_3H_7$ | n-$C_4H_9$ | n-$C_4H_9$ | n-$C_4H_9$ | n-$C_4H_9$ | oil |
| 8. | 2-$BrC_6H_4$ | n-$C_3H_7$ | n-$C_3H_7$ | n-$C_3H_7$ | n-$C_3H_7$ | oil |
| 9. | 3,4-$ClC_6H_3$ | n-$C_3H_7$ | n-$C_3H_7$ | n-$C_3H_7$ | n-$C_3H_7$ | oil |
| 10. | n-$C_3H_7$ | $CH_3$ | 4-$CH_3OC_6H_4$ | n-$C_3H_7$ | n-$C_3H_7$ | oil |
| 11. | n-$C_3H_7$ | $CH_3$ | 4-$CH_3OC_6H_4$ | n-$C_4H_9$ | n-$C_4H_9$ | oil |
| 12. | n-$C_3H_7$ | $CH_3$ | 2-pyridyl | n-$C_3H_7$ | n-$C_3H_7$ | |
| 13. | n-$C_3H_7$ | $CH_3$ | 2-pyridyl | n-$C_5H_{11}$ | n-$C_5H_{11}$ | oil |
| 14. | n-$C_3H_7$ | $CH_3$ | 2-$CH_3C_6H_4$ | n-$C_3H_7$ | n-$C_3H_7$ | oil |
| 15. | n-$C_3H_7$ | $CH_3$ | 2-$CH_3C_6H_4$ | n-$C_5H_{11}$ | n-$C_5H_{11}$ | oil |
| 16. | n-$C_3H_7$ | $CH_3$ | 4-$ClC_6H_4$ | n-$C_3H_7$ | n-$C_3H_7$ | oil |
| 17. | n-$C_3H_7$ | $CH_3$ | 4-$ClC_6H_4$ | n-$C_5H_{11}$ | n-$C_5H_{11}$ | oil |
| 18. | n-$C_3H_7$ | $CH_3$ | 2-$OCH_3$,4-$ClC_6H_3$ | n-$C_4H_9$ | n-$C_4H_9$ | oil |
| 19. | n-$C_3H_7$ | $CH_3$ | 2,4-$FC_6H_3$ | n-$C_3H_7$ | n-$C_3H_7$ | oil |
| 20. | n-$C_3H_7$ | $CH_3$ | 3,4-$ClC_6H_3$ | n-$C_3H_7$ | n-$C_3H_7$ | oil |
| 21. | n-$C_3H_7$ | $CH_3$ | 3,4-$ClC_6H_3$ | n-$C_4H_9$ | n-$C_4H_9$ | oil |
| 22. | n-$C_3H_7$ | $CH_3$ | 2,4-$ClC_6H_3$ | n-$C_3H_7$ | n-$C_3H_7$ | |
| 23. | n-$C_3H_7$ | $CH_3$ | 2,4-$ClC_6H_3$ | n-$C_4H_9$ | n-$C_4H_9$ | oil |
| 24. | n-$C_3H_7$ | n-$C_4H_9$ | $C_6H_5$ | n-$C_3H_7$ | n-$C_3H_7$ | oil |
| 25. | n-$C_3H_7$ | n-$C_3H_7$ | $C_6H_5$ | n-$C_3H_7$ | n-$C_3H_7$ | oil |
| 26. | n-$C_3H_7$ | $C_2H_5$ | $C_6H_5$ | n-$C_3H_7$ | n-$C_3H_7$ | oil |
| 27. | n-$C_3H_7$ | $CH_3$ | $C_6H_5$ | n-$C_3H_7$ | n-$C_3H_7$ | oil |
| 28. | n-$C_3H_7$ | i-$C_3H_7$ | i-$C_3H_7$ | n-$C_4H_9$ | n-$C_4H_9$ | oil |
| 29. | n-$C_3H_7$ | i-$C_3H_7$ | i-$C_3H_7$ | $C_2H_5$ | $C_2H_5$ | oil |
| 30. | n-$C_3H_7$ | $CH_3$ | 3,4-F—$C_6H_3$ | n-$C_3H_7$ | n-$C_3H_7$ | oil |
| 31. | n-$C_3H_7$ | $CH_3$ | 3-Cl,4-F—$C_6H_3$ | n-$C_3H_7$ | n-$C_3H_7$ | oil |
| 32. | n-$C_3H_7$ | $CH_3$ | 4-$FC_6H_4$ | n-$C_3H_7$ | n-$C_3H_7$ | oil |
| 33. | n-$C_3H_7$ | $CH_3$ | 2-$FC_6H_4$ | n-$C_3H_7$ | n-$C_3H_7$ | oil |
| 34. | n-$C_3H_7$ | $CH_3$ | 2,5-$ClC_6H_3$ | n-$C_3H_7$ | n-$C_3H_7$ | oil |
| 35. | n-$C_3H_7$ | $CH_3$ | 2,3-$ClC_6H_3$ | n-$C_3H_7$ | n-$C_3H_7$ | oil |
| 36. | n-$C_3H_7$ | $CH_3$ | 4-$OCH_3C_6H_4$ | n-$C_3H_7$ | n-$C_3H_7$ | oil |
| 37. | n-$C_3H_7$ | $CH_3$ | 2,4-$BrC_6H_3$ | n-$C_3H_7$ | n-$C_3H_7$ | oil |
| 38. | n-$C_3H_7$ | $CH_3$ | 2,4-$ClC_6H_3$ | n-$C_3H_7$ | n-$C_3H_7$ | oil |
| 39. | n-$C_3H_7$ | $CH_3$ | 2-$CH_3$,4-$BrC_6H_3$ | n-$C_3H_7$ | n-$C_3H_7$ | oil |
| 40. | n-$C_3H_7$ | $CH_3$ | 3-pyridyl | n-$C_3H_7$ | n-$C_3H_7$ | oil |
| 41. | n-$C_3H_7$ | $CH_3$ | 4-$CNC_6H_4$ | n-$C_3H_7$ | n-$C_3H_7$ | oil |
| 42. | n-$C_3H_7$ | $CH_3$ | 3,4-$OCH_3C_6H_3$ | n-$C_3H_7$ | n-$C_3H_7$ | oil |
| 43. | n-$C_3H_7$ | $CH_3$ | 3,5-$OCH_3C_6H_3$ | n-$C_3H_7$ | n-$C_3H_7$ | oil |
| 44. | n-$C_3H_7$ | $CH_3$ | 3-$NO_2C_6H_4$ | n-$C_3H_7$ | n-$C_3H_7$ | oil |
| 45. | n-$C_3H_7$ | $CH_3$ | 4-F—$C_6H_4$ | $CH_3$ | 4-F—$C_6H_4$ | oil |
| 46. | n-$C_3H_7$ | $(CH_2)_2OCH_3$ | $(CH_2)_2OCH_3$ | n-$C_3H_7$ | n-$C_3H_7$ | oil |
| 47. | n-$C_3H_7$ | $CH_3$ | 2,3,4-F—$C_6H_2$ | n-$C_3H_7$ | n-$C_3H_7$ | oil |
| 48. | n-$C_3H_7$ | $CH_3$ | 2,4,5-F—$C_6H_2$ | n-$C_3H_7$ | n-$C_3H_7$ | oil |

TABLE I-continued $$R_1S-\overset{\overset{O}{\|}}{\underset{\underset{R_4}{|}}{P}}\overset{R_2}{\underset{R_5}{-N}}$$

| Compound No. | $R_1$ | $R_2$ | $R_3$ | $R_4$ | $R_5$ | m.p. °C. or $n_D^{30}$ |
|---|---|---|---|---|---|---|
| 49. | n-C$_3$H$_7$ | C$_2$H$_5$ | i-C$_4$H$_9$ | C$_2$H$_5$ | i-C$_4$H$_9$ | oil |
| 50. | n-C$_3$H$_7$ | n-C$_4$H$_9$ | i-C$_4$H$_9$ | n-C$_4$H$_9$ | i-C$_4$H$_9$ | oil |
| 51. | n-C$_3$H$_7$ | C$_2$H$_5$ | i-C$_5$H$_{11}$ | C$_2$H$_5$ | i-C$_5$H$_{11}$ | oil |
| 52. | n-C$_3$H$_7$ | n-C$_4$H$_9$ | i-C$_5$H$_{11}$ | n-C$_4$H$_9$ | i-C$_5$H$_{11}$ | oil |
| 53. | n-C$_3$H$_7$ | CH$_3$ | 2,3,5,6-F—C$_6$H | n-C$_3$H$_7$ | n-C$_3$H$_7$ | oil |
| 54. | n-C$_3$H$_7$ | C$_2$H$_5$ | 4-F—C$_6$H$_4$ | n-C$_3$H$_7$ | n-C$_3$H$_7$ | oil |
| 55. | n-C$_3$H$_7$ | n-C$_4$H$_9$ | 4-F—C$_6$H$_4$ | n-C$_3$H$_7$ | n-C$_3$H$_7$ | oil |
| 56. | n-C$_3$H$_7$ | CH$_3$ | 2-(i-C$_3$H$_7$)—C$_6$H$_4$ | n-C$_3$H$_7$ | n-C$_3$H$_7$ | oil |
| 57. | n-C$_3$H$_7$ | n-C$_3$H$_7$ | 2-(i-C$_3$H$_7$)—C$_6$H$_4$ | n-C$_3$H$_7$ | n-C$_3$H$_7$ | oil |
| 58. | n-C$_3$H$_7$ | CH$_3$ | 4-(i-C$_3$H$_7$)—C$_6$H$_4$ | n-C$_3$H$_7$ | n-C$_3$H$_7$ | oil |
| 59. | n-C$_3$H$_7$ | n-C$_3$H$_7$ | 4-(i-C$_3$H$_7$)—C$_6$H$_4$ | n-C$_3$H$_7$ | n-C$_3$H$_7$ | oil |
| 60. | 3-Cl—C$_6$H$_4$ | n-C$_3$H$_7$ | n-C$_3$H$_7$ | n-C$_3$H$_7$ | n-C$_3$H$_7$ | oil |
| 61. | n-C$_3$H$_7$ | n-C$_3$H$_7$ | 2-CH$_3$,4-ClC$_6$H$_3$ | n-C$_3$H$_7$ | n-C$_3$H$_7$ | oil |
| 62. | n-C$_3$H$_7$ | CH$_3$ | 2-CH$_3$,4-ClC$_6$H$_3$ | n-C$_3$H$_7$ | n-C$_3$H$_7$ | oil |
| 63. | C$_6$H$_5$ | n-C$_3$H$_7$ | n-C$_3$H$_7$ | n-C$_3$H$_7$ | n-C$_3$H$_7$ | oil |
| 64. | n-C$_3$H$_7$ | CH$_3$ | 2-CH$_3$,4-F—C$_6$H$_3$ | n-C$_3$H$_7$ | n-C$_3$H$_7$ | oil |
| 65. | n-C$_3$H$_7$ | CH$_3$ | 2-CH$_3$,4-CH$_3$O—C$_6$H$_3$ | n-C$_3$H$_7$ | n-C$_3$H$_7$ | oil |
| 66. | n-C$_3$H$_7$ | CH$_3$ | 3-Cl,4-CF$_3$O—C$_6$H$_3$ | n-C$_3$H$_7$ | n-C$_3$H$_7$ | oil |
| 67. | n-C$_3$H$_7$ | CH$_3$ | 2-CH$_3$,5-F—C$_6$H$_3$ | n-C$_3$H$_7$ | n-C$_3$H$_7$ | oil |
| 68. | n-C$_3$H$_7$ | C$_2$H$_5$ | C$_2$H$_5$ | C$_2$H$_5$ | C$_2$H$_5$ | 105–114° C. |
| 69. | n-C$_4$H$_9$ | C$_2$H$_5$ | C$_2$H$_5$ | C$_2$H$_5$ | C$_2$H$_5$ | 146.5–151° C. |
| 70. | C$_2$H$_5$ | n-C$_3$H$_7$ | n-C$_3$H$_7$ | n-C$_3$H$_7$ | n-C$_3$H$_7$ | 1.4784 |
| 71. | n-C$_3$H$_7$ | n-C$_3$H$_7$ | n-C$_3$H$_7$ | n-C$_3$H$_7$ | n-C$_3$H$_7$ | 1.4781 |
| 72. | C$_2$H$_5$ | —(CH$_2$)$_5$— | | n-C$_3$H$_7$ | n-C$_3$H$_7$ | 1.4970 |
| 73. | n-C$_3$H$_7$ | —(CH$_2$)$_5$— | | n-C$_3$H$_7$ | n-C$_3$H$_7$ | 1.4957 |
| 74. | n-C$_4$H$_9$ | —(CH$_2$)$_5$— | | n-C$_3$H$_7$ | n-C$_3$H$_7$ | 1.4941 |
| 75. | C$_2$H$_5$ | CH$_2$CH=CH$_2$ | CH$_2$CH=CH$_2$ | n-C$_3$H$_7$ | n-C$_3$H$_7$ | 1.4930 |
| 76. | n-C$_3$H$_7$ | CH$_2$CH=CH$_2$ | CH$_2$CH=CH$_2$ | n-C$_3$H$_7$ | n-C$_3$H$_7$ | 1.4918 |
| 77. | n-C$_4$H$_9$ | CH$_2$CH=CH$_2$ | CH$_2$CH=CH$_2$ | n-C$_3$H$_7$ | n-C$_3$H$_7$ | 1.4899 |
| 78. | C$_6$H$_5$ | n-C$_3$H$_7$ | n-C$_3$H$_7$ | n-C$_3$H$_7$ | n-C$_3$H$_7$ | 1.5257 |
| 79. | i-C$_3$H$_7$ | n-C$_3$H$_7$ | n-C$_3$H$_7$ | n-C$_3$H$_7$ | n-C$_3$H$_7$ | 1.4762 |
| 80. | sec-C$_4$H$_9$ | n-C$_3$H$_7$ | n-C$_3$H$_7$ | n-C$_3$H$_7$ | n-C$_3$H$_7$ | 1.4760 |
| 81. | C(CH$_3$)$_2$C$_2$H$_5$ | n-C$_3$H$_7$ | n-C$_3$H$_7$ | n-C$_3$H$_7$ | n-C$_3$H$_7$ | 1.4789 |
| 82. | C$_2$H$_5$ | n-C$_4$H$_9$ | n-C$_4$H$_9$ | n-C$_4$H$_9$ | n-C$_4$H$_9$ | 1.4742 |
| 83. | n-C$_4$H$_9$ | n-C$_4$H$_9$ | n-C$_4$H$_9$ | n-C$_4$H$_9$ | n-C$_4$H$_9$ | 1.4733 |
| 84. | C$_2$H$_5$ | C$_2$H$_5$ | C$_2$H$_5$ | n-C$_4$H$_9$ | n-C$_4$H$_9$ | 1.4793 |
| 85. | n-C$_3$H$_7$ | C$_2$H$_5$ | C$_2$H$_5$ | n-C$_4$H$_9$ | n-C$_4$H$_9$ | 1.4779 |
| 86. | n-C$_4$H$_9$ | C$_2$H$_5$ | C$_2$H$_5$ | n-C$_4$H$_9$ | n-C$_4$H$_9$ | 1.4764 |
| 87. | i-C$_3$H$_7$ | C$_2$H$_5$ | C$_2$H$_5$ | n-C$_4$H$_9$ | n-C$_4$H$_9$ | 1.4756 |
| 88. | C$_2$H$_5$ | C$_2$H$_5$ | n-C$_4$H$_9$ | n-C$_3$H$_7$ | n-C$_3$H$_7$ | 1.4769 |
| 89. | n-C$_3$H$_7$ | C$_2$H$_5$ | n-C$_4$H$_9$ | n-C$_3$H$_7$ | n-C$_3$H$_7$ | 1.4762 |
| 90. | n-C$_4$H$_9$ | C$_2$H$_9$ | n-C$_4$H$_9$ | n-C$_3$H$_7$ | n-C$_3$H$_7$ | 1.4752 |
| 91. | i-C$_3$H$_7$ | C$_2$H$_5$ | n-C$_4$H$_9$ | n-C$_3$H$_7$ | n-C$_3$H$_7$ | 1.4745 |
| 92. | n-C$_3$H$_7$ | —(CH$_2$)$_6$— | | C$_2$H$_5$ | C$_2$H$_5$ | 1.5039 |
| 93. | n-C$_4$H$_9$ | —(CH$_2$)$_6$— | | C$_2$H$_5$ | C$_2$H$_5$ | 1.5013 |
| 94. | C$_6$H$_5$CH$_2$— | C$_2$H$_5$ | C$_2$H$_5$ | C$_2$H$_5$ | C$_2$H$_5$ | 1.5349 |
| 95. | C$_6$H$_5$CH$_2$— | n-C$_3$H$_7$ | n-C$_3$H$_7$ | n-C$_3$H$_7$ | n-C$_3$H$_7$ | 1.5192 |
| 96. | C$_2$H$_5$ | | ![cyclohexyl with CH$_3$ and C$_2$H$_5$] | n-C$_3$H$_7$ | n-C$_3$H$_7$ | 1.4910 |
| 97. | i-C$_3$H$_7$ | | ![cyclohexyl with CH$_3$ and C$_2$H$_5$] | n-C$_3$H$_7$ | n-C$_3$H$_7$ | 1.4869 |
| 98. | sec-C$_4$H$_5$ | | ![cyclohexyl with CH$_3$ and C$_2$H$_5$] | n-C$_3$H$_7$ | n-C$_3$H$_7$ | 1.4880 |
| 99. | CH$_2$=CHCH$_2$— | n-C$_3$H$_7$ | n-C$_3$H$_7$ | n-C$_3$H$_7$ | n-C$_3$H$_7$ | 1.4870 |

TABLE I-continued $$R_1S-\overset{\overset{O}{\|}}{\underset{\underset{R_4}{N}}{P}}-\overset{R_2}{\underset{R_3}{N}}$$

| Compound No. | $R_1$ | $R_2$ | $R_3$ | $R_4$ | $R_5$ | m.p. °C. or $n_D^{30}$ |
|---|---|---|---|---|---|---|
| 100. | $CH_2=CHCH_2-$ | | $-(CH_2)_6-$ | $n-C_3H_7$ | $n-C_3H_7$ | 1.5163 |
| 101. | $i-C_3H_7$ | | $-(CH_2)_6-$ | $C_2H_5$ | $C_2H_5$ | 1.5029 |
| 102. | $sec-C_4H_9$ | $C_2H_5$ | $C_2H_5$ | $n-C_4H_9$ | $n-C_4H_9$ | 1.4772 |
| 103. | $i-C_3H_7$ | $C_2H_5$ | $C_2H_5$ | $C_2H_5$ | $C_2H_5$ | 1.4800 |
| 104. | $sec-C_4H_9$ | $C_2H_9$ | $C_2H_5$ | $C_2H_5$ | $C_2H_5$ | 1.4809 |
| 105. | $3-C_6H_{13}$ | $C_2H_5$ | $C_2H_5$ | $C_2H_5$ | $C_2H_5$ | 1.4862 |
| 106. | $t-C_4H_9$ | $CH_3$ | $CH_3$ | $n-C_4H_9$ | $n-C_4H_9$ | 1.4777 |
| 107. | $C_2H_5$ | $CH_3$ | $CH_3$ | $n-C_4H_9$ | $n-C_4H_9$ | 1.4799 |
| 108. | $n-C_3H_7$ | $CH_3$ | $CH_3$ | $n-C_4H_9$ | $n-C_4H_9$ | 1.4790 |
| 109. | $i-C_3H_7$ | $CH_3$ | $CH_3$ | $n-C_4H_9$ | $n-C_4H_9$ | 1.4765 |
| 110. | $n-C_4H_9$ | $CH_3$ | $CH_3$ | $n-C_4H_9$ | $n-C_4H_9$ | 1.4774 |
| 111. | $sec-C_4H_9$ | $CH_3$ | $CH_3$ | $n-C_4H_9$ | $n-C_4H_9$ | 1.4770 |
| 112. | $CH_2=CHCH_2-$ | $CH_3$ | $CH_3$ | $n-C_4H_9$ | $n-C_4H_9$ | 1.4880 |
| 113. | $C_6H_5CH_2-$ | $CH_3$ | $CH_3$ | $n-C_4H_9$ | $n-C_4H_9$ | 1.5173 |
| 114. | $sec-C_4H_9$ | $C_2H_5$ | $n-C_4H_9$ | $n-C_3H_7$ | $n-C_3H_7$ | 1.4754 |
| 115. | $CH_2=CHCH_2-$ | $C_2H_5$ | $n-C_4H_9$ | $n-C_3H_7$ | $n-C_3H_7$ | 1.4820 |
| 116. | $n-C_6H_{13}$ | $n-C_3H_7$ | $n-C_3H_7$ | $n-C_3H_7$ | $n-C_3H_7$ | 1.4755 |
| 117. |  | $CH_3$ | $CH_3$ | $n-C_4H_9$ | $n-C_4H_9$ | 1.4932 |
| 118. |  | $n-C_3H_7$ | $n-C_3H_7$ | $n-C_3H_7$ | $n-C_3H_7$ | 1.4904 |
| 119. | $C_2H_5$ | $CH_3$ | $C_6H_5$ | $n-C_3H_7$ | $n-C_3H_7$ | 1.5343 |
| 120. | $i-C_3H_7$ | $CH_3$ | $C_6H_5$ | $n-C_3H_7$ | $n-C_3H_7$ | 1.5287 |
| 121. | $n-C_4H_9$ | $CH_3$ | $C_6H_5$ | $n-C_3H_7$ | $n-C_3H_7$ | 1.5273 |
| 122. | $sec-C_4H_9$ | $CH_3$ | $C_6H_5$ | $n-C_3H_7$ | $n-C_3H_7$ | 1.5264 |
| 123. | $C_2H_5$ | $n-C_3H_7$ | $n-C_3H_7$ | $n-C_4H_9$ | $n-C_4H_9$ | 1.4766 |
| 124. | $n-C_3H_7$ | $n-C_3H_7$ | $n-C_3H_7$ | $n-C_4H_9$ | $n-C_4H_9$ | 1.4754 |
| 125. | $i-C_3H_7$ | $n-C_3H_7$ | $n-C_3H_7$ | $n-C_4H_9$ | $n-C_4H_9$ | 1.4745 |
| 126. | $n-C_4H_9$ | $n-C_3H_7$ | $n-C_3H_7$ | $n-C_4H_9$ | $n-C_4H_9$ | 1.4753 |
| 127. | $sec-C_4H_9$ | $n-C_3H_7$ | $n-C_3H_7$ | $n-C_4H_9$ | $n-C_4H_9$ | 1.4742 |
| 128. | $t-C_4H_9$ | $n-C_3H_7$ | $n-C_3H_7$ | $n-C_4H_9$ | $n-C_4H_9$ | 1.4757 |
| 129. | $CH_2=CHCH_2-$ | $n-C_3H_7$ | $n-C_3H_7$ | $n-C_4H_9$ | $n-C_4H_9$ | 1.4840 |
| 130. | $n-C_5H_{11}$ | $n-C_3H_7$ | $n-C_3H_7$ | $n-C_4H_9$ | $n-C_4H_9$ | 1.4143 |
| 131. | $n-C_5H_{11}$ | $n-C_3H_7$ | $n-C_3H_7$ | $n-C_3H_7$ | $n-C_3H_7$ | 1.4713 |
| 132. | $n-C_5H_{11}$ | $n-C_4H_9$ | $n-C_4H_9$ | $n-C_4H_9$ | $n-C_4H_9$ | 1.4737 |
| 133. | $n-C_5H_{11}$ | $C_2H_5$ | $n-C_4H_9$ | $n-C_3H_7$ | $n-C_3H_7$ | 1.4742 |
| 134. | $n-C_6H_{13}$ | $n-C_4H_9$ | $n-C_4H_9$ | $n-C_4H_9$ | $n-C_4H_9$ | 1.4725 |
| 135. | $n-C_6H_{13}$ | $C_2H_5$ | $n-C_4H_9$ | $n-C_3H_7$ | $n-C_3H_7$ | 1.4750 |
| 136. |  | $n-C_4H_9$ | $n-C_4H_9$ | $n-C_4H_9$ | $n-C_4H_9$ | 1.4853 |
| 137. |  | $C_2H_5$ | $n-C_4H_9$ | $n-C_3H_7$ | $n-C_3H_7$ | 1.4904 |
| 138. | $C_2H_5$ | $C_2H_5$ | $n-C_4H_9$ | $C_2H_5$ | $C_2H_5$ | 1.4803 |
| 139. | $n-C_3H_7$ | $C_2H_5$ | $n-C_4H_9$ | $C_2H_5$ | $C_2H_5$ | 1.4791 |
| 140. | $i-C_3H_7$ | $C_2H_5$ | $n-C_4H_9$ | $C_2H_5$ | $C_2H_5$ | 1.4778 |
| 141. | $n-C_4H_9$ | $C_2H_5$ | $n-C_4H_9$ | $C_2H_5$ | $C_2H_5$ | 1.4786 |
| 142. | $i-C_3H_7$ | $C_2H_5$ | $n-C_4H_9$ | $C_2H_5$ | $C_2H_5$ | 1.4787 |
| 143. | $C_6H_5CH(CH_3)-$ | $C_2H_5$ | $n-C_4H_9$ | $C_2H_5$ | $C_2H_5$ | 1.5175 |
| 144. | $C_2H_5$ | $C_2H_5$ | $C_2H_5$ | $n-C_3H_7$ | $n-C_3H_7$ | 1.4809 |
| 145. | $n-C_3H_7$ | $C_2H_5$ | $C_2H_5$ | $n-C_3H_7$ | $n-C_3H_7$ | 1.4799 |

A cyclic compound made as in Example 2 is (Compound No. 146)

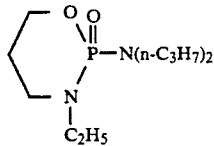

Herbicidal Activity Tests

Compounds 1 to 67 in Table I and Compound No. 146 were tested for herbicidal activity as follows:

The herbicidal effect was observed by comparing the extent of weed control in test flats treated with the compounds against that occurring in similar non-treated control flats. All were applied at 3.57 lb/A (4 kg/ha) to pre-emergence and post-emergence screening flats. An 80 gal/A (748.3 1/ha) spray volume was utilized. Post-emergence flats were seeded 12 days prior to treatment. Pre-emergence flats were seeded one day prior to treatment. Overhead watering of pre-emergence flats and soil surface watering of post-emergence flats, so as to avoid wetting the foliage, were carried out for the duration of the test.

Weed seeds were planted in a flat at a seed depth of 0.5 inch (1.3 cm). Soil for flats was prepared using loam soil fortified with 17-17-17 fertilizer ($N-P_2O_5-K_2O$ on a weight basis) and Captan 80W fungicide. The test weeds were as follows:

| COMMON NAME | SCIENTIFIC NAME |
|---|---|
| green foxtail | *Setaria viridis* |
| watergrass | *Echinochloa crusgalli* |
| wild oat | *Avena fatua* |

| COMMON NAME | SCIENTIFIC NAME |
|---|---|
| annual morning glory | *Ipomoea purpurea* |
| velvetleaf | *Abutilon theophrasti* |
| wild mustard | *Brassica kaber* |
| yellow nutsedge | *Cyperus esculentus* |

The spray solutions were prepared by dissolving 240 mg of test compound in 20 ml of acetone containing 1% polyoxyethylene sorbitan monolaurate emulsifier, then adding 20 ml of water to the resulting solution. The spray solutions were applied using a linear spray table. Pre-emergence flats are raised to the level of the post-emergence foliage canopy by setting the flats on a wooden block.

The degree of weed control was visually assessed and recorded as percentage control compared to the growth of the same species in an untreated check flat of the same age. The rating scale ranges from 0 to 100%, where 0 equals no effect with plant growth equal to the untreated control, and 100 equals complete kill.

Ratings were taken in pre-emergence tests approximately 18 days after treatment (DAT). In post-emergence tests, ratings were taken at two intervals. On the sixth day after treatment, overall control was rated, as an indication of total vegetative control, or "contact and burn" activity. Approximately 18 days after treatment, the tests were rated for overall post-emergence activity.

Results are listed in Table II below, expressed as average control of the three grassy (GR) (wild oat, watergrass, foxtail) and three broadleaf weeds (BL) (morning glory, mustard, velvetleaf), and of nutsedge (NS).

TABLE II

| | % Control, 3.57 kg/ha | | | | | | | | |
|---|---|---|---|---|---|---|---|---|---|
| | Pre-emergence | | | Post-emergence | | | | | |
| Compound | 18 DAT | | | 6 DAT | | | 18 DAT | | |
| No. | GR avg. | BL avg. | NS | GR avg. | BL avg. | NS | GR avg. | BL avg. | NS |
| 1. | 2 | 50 | 0 | 90 | 90 | 10 | 85 | 100 | 5 |
| 2. | 33 | 33 | 0 | 80 | 100 | 20 | 57 | 100 | 10 |
| 3. | 0 | 100 | 0 | 80 | 80 | 5 | 70 | 100 | 0 |
| 4. | 0 | 0 | 0 | 70 | 50 | 0 | 77 | 45 | 0 |
| 5. | 0 | 0 | 0 | 40 | 40 | 0 | 27 | 33 | 0 |
| 6. | 0 | 0 | 0 | 70 | 80 | 0 | 53 | 93 | 0 |
| 7. | 0 | 0 | 0 | 90 | 90 | 10 | 93 | 100 | 0 |
| 8. | 0 | 0 | 0 | 30 | 50 | 0 | 13 | 55 | 0 |
| 9. | 0 | 0 | 0 | 50 | 50 | 0 | 47 | 83 | 0 |
| 10. | 0 | 0 | 9 | 30 | 80 | 10 | 23 | 80 | 0 |
| 11. | 0 | 0 | 9 | 30 | 60 | 10 | 50 | 70 | 0 |
| 12. | 0 | 0 | 0 | 30 | 80 | 0 | 30 | 80 | 0 |
| 13. | 17 | 33 | 0 | 80 | 90 | 10 | 83 | 93 | 0 |
| 14. | 30 | 33 | 0 | 60 | 60 | 5 | 73 | 67 | 0 |
| 15. | 0 | 0 | 0 | 50 | 80 | 5 | 47 | 60 | 0 |
| 16. | 0 | 0 | 0 | 33 | 43 | 0 | 47 | 73 | 0 |
| 17. | 57 | 33 | 0 | 80 | 50 | 10 | 33 | 43 | 0 |
| 18. | 0 | 0 | 0 | 10 | 30 | 0 | 30 | 60 | 0 |
| 19. | 0 | 0 | — | 0 | 0 | 0 | 63 | 100 | 0 |
| 20. | 0 | 0 | 0 | 20 | 50 | 5 | 13 | 67 | 0 |
| 21. | 0 | 0 | 0 | 0 | 20 | 0 | 17 | 40 | 0 |
| 22. | 0 | 0 | 0 | 50 | 60 | 10 | 53 | 60 | 0 |
| 23. | 0 | 0 | 0 | 20 | 50 | 0 | 13 | 43 | 0 |
| 24. | 0 | 33 | 0 | 30 | 80 | 10 | 23 | 73 | 0 |
| 25. | 0 | 33 | 0 | 50 | 50 | 0 | 67 | 67 | 0 |
| 26. | 7 | 33 | 0 | 20 | 50 | 0 | 10 | 50 | 0 |
| 27. | 0 | 0 | 0 | 20 | 30 | 0 | 40 | 83 | 5 |
| 28. | 0 | 0 | 0 | 10 | 30 | 0 | 7 | 67 | 0 |
| 29. | 0 | 0 | 0 | 10 | 10 | 0 | 7 | 33 | 0 |
| 30. | 0 | 0 | 0 | 5 | 80 | 0 | 0 | 97 | 0 |
| 31. | 0 | 0 | 0 | 10 | 20 | 0 | 5 | 60 | 0 |
| 32. | 0 | 0 | 0 | 10 | 20 | 0 | 3 | 73 | 0 |
| 33. | 0 | 0 | 0 | 5 | 20 | 0 | 0 | 47 | 0 |
| 34. | 0 | 0 | 0 | 50 | 80 | 0 | 10 | 93 | 0 |

TABLE II-continued

| | % Control, 3.57 kg/ha | | | | | | | | |
|---|---|---|---|---|---|---|---|---|---|
| | Pre-emergence | | | Post-emergence | | | | | |
| Compound | 18 DAT | | | 6 DAT | | | 18 DAT | | |
| No. | GR avg. | BL avg. | NS | GR avg. | BL avg. | NS | GR avg. | BL avg. | NS |
| 35. | 0 | 0 | 0 | 20 | 20 | 0 | 33 | 33 | 0 |
| 36. | 0 | 0 | 0 | 10 | 100 | 0 | 10 | 100 | 0 |
| 37. | 0 | 0 | 0 | 20 | 80 | 0 | 10 | 83 | 0 |
| 38. | 0 | 0 | 0 | — | — | — | 40 | 100 | 0 |
| 39. | 0 | 0 | 0 | — | — | — | 67 | 93 | 80 |
| 40. | 0 | 0 | 0 | — | — | — | 10 | 70 | 0 |
| 41. | 0 | 0 | 0 | 0 | 0 | 0 | 17 | 60 | 0 |
| 42. | 0 | 0 | 0 | 20 | 50 | 0 | 23 | 83 | 0 |
| 43. | 0 | 0 | 0 | 10 | 20 | 0 | 10 | 70 | 0 |
| 44. | 0 | 0 | 0 | — | — | — | 10 | 53 | 0 |
| 45. | 0 | 0 | 0 | 50 | 90 | 0 | 75 | 92 | 10 |
| 46. | 0 | 0 | 0 | 30 | 60 | 0 | 47 | 73 | 0 |
| 47. | 0 | 0 | 0 | 85 | 100 | 0 | 40 | 98 | 0 |
| 48. | 0 | 0 | 0 | 80 | 90 | 0 | 40 | 80 | 0 |
| 49. | 0 | 0 | 0 | 80 | 100 | 0 | 47 | 100 | 0 |
| 50. | 0 | 0 | 0 | 90 | 85 | 0 | 77 | 70 | 0 |
| 51. | 0 | 8 | 0 | 70 | 95 | 0 | 45 | 100 | 0 |
| 52. | 0 | 0 | 0 | 30 | 90 | 0 | 0 | 86 | 0 |
| 53. | 0 | 10 | 0 | 75 | 100 | 0 | 43 | 100 | 0 |
| 54. | 0 | 8 | 0 | 75 | 100 | 0 | 28 | 100 | 0 |
| 55. | 13 | 3 | 5 | 40 | 90 | 0 | 6 | 86 | 0 |
| 56. | 31 | 6 | 0 | 30 | 85 | 0 | 6 | 90 | 0 |
| 57. | 0 | 0 | 0 | 20 | 70 | 0 | 16 | 60 | 0 |
| 58. | 0 | 0 | 0 | 50 | 70 | 0 | 6 | 61 | 0 |
| 59. | 0 | 0 | 0 | 10 | 50 | 0 | 6 | 55 | 0 |
| 60. | 0 | 13 | 0 | 40 | 75 | 0 | 16 | 73 | 0 |
| 61. | 0 | 3 | 0 | 50 | 80 | 0 | 38 | 76 | 0 |
| 62. | 0 | 0 | 0 | 30 | 75 | 0 | 33 | 76 | 0 |
| 63. | 0 | 3 | 0 | 60 | 80 | 0 | 43 | 91 | 0 |
| 64. | 3 | 0 | 0 | 50 | 85 | 0 | 16 | 93 | 5 |
| 65. | 0 | 0 | 0 | 90 | 70 | 0 | 13 | 76 | 0 |
| 66. | 0 | 10 | 0 | 60 | 90 | 0 | 16 | 98 | 5 |
| 67. | 0 | 16 | 0 | 30 | 95 | 0 | 0 | 100 | 0 |

Compounds 68 to 145 in Table I were tested generally similarly to Compounds No. 1 to 67 with the following differences: The rate of application was 2 lb/acre (2.24 kg/ha), no 6-day evaluations were made, and the weeds were:

Four grassy weeds: wild oat, watergrass, green foxtail and crabgrass (*Digitaria sanguinalis*);

Three broadleaf weeds: wild mustard, redroot pigweed (*Amaranthus retroflexus*) and curly dock (*Rumex crispus*).

Ratings were taken 2-3 weeks after treatment. Results of these tests were given in Table III.

TABLE III

| | % Control, 2.24 kg/ha | | | |
|---|---|---|---|---|
| Compound | Pre-Emergence | | Post-Emergence | |
| No. | GR Avg. | BL Avg. | GR Avg. | BL Avg. |
| 68. | — | — | 40 | 87 |
| 69. | 13 | 0 | 30 | 87 |
| 70. | 5 | 10 | 82 | 99 |
| 71. | 27 | 57 | 64 | 99 |
| 72. | — | — | 50 | 86 |
| 73. | — | — | 55 | 87 |
| 74. | — | — | 47 | 100 |
| 75. | 0 | 0 | 62 | 98 |
| 76. | 0 | 0 | 61 | 99 |
| 77. | 0 | 0 | 53 | 99 |
| 78. | 0 | 0 | 50 | 98 |
| 79. | 35 | 50 | 85 | 99 |
| 80. | 25 | 53 | 80 | 100 |
| 81. | 0 | 0 | 66 | 83 |
| 82. | 0 | 0 | 75 | 99 |
| 83. | 5 | 7 | 82 | 99 |
| 84. | 5 | 13 | 75 | 99 |
| 85. | 12 | 10 | 89 | 99 |
| 86. | 5 | 7 | 77 | 99 |
| 87. | 5 | 12 | 62 | 99 |
| 88. | 0 | 0 | 89 | 96 |
| 89. | 0 | 7 | 90 | 100 |
| 90. | 0 | 7 | 86 | 100 |
| 91. | 0 | 3 | 84 | 99 |
| 92. | — | — | 62 | 86 |
| 93. | — | — | 73 | 99 |
| 94. | — | — | 30 | 70 |
| 95. | 5 | 13 | 55 | 80 |
| 96. | 0 | 10 | 65 | 67 |
| 97. | 0 | 20 | 67 | 86 |
| 98. | 0 | 33 | 61 | 90 |
| 99. | 22 | 37 | 58 | 99 |
| 100. | — | — | 63 | 95 |
| 101. | — | — | 69 | 100 |
| 102. | 30 | 40 | 70 | 99 |
| 103. | — | — | 67 | 73 |
| 104. | — | — | 77 | 87 |
| 105. | — | — | 54.5 | 73 |
| 106. | — | — | 65 | 91 |
| 107. | — | — | 64 | 98 |
| 108. | 15 | 13 | 76 | 98 |
| 109. | 23 | 20 | 85 | 98 |
| 110. | — | — | 93 | 98 |
| 111. | 10 | 10 | 72 | 99 |
| 112. | — | — | 56 | 87 |
| 113. | — | — | 48 | 83 |
| 114. | 0 | 0 | 56 | 93 |
| 115. | 0 | 0 | 70 | 86 |
| 116. | 0 | 10 | 53 | 96 |
| 117. | 0 | 0 | 50 | 77 |
| 118. | 0 | 0 | 30 | 63 |
| 119. | 0 | 0 | 30 | 67 |
| 120. | — | — | 50 | 71 |
| 121. | — | — | 59 | 72 |
| 122. | — | — | 56 | 79 |
| 123. | 0 | 0 | 65 | 89 |
| 124. | 0 | 0 | 67 | 79 |

TABLE III-continued

| Compound No. | % Control, 2.24 kg/ha | | | |
|---|---|---|---|---|
| | Pre-Emergence | | Post-Emergence | |
| | GR Avg. | BL Avg. | GR Avg. | BL Avg. |
| 125. | 0 | 0 | 59 | 70 |
| 126. | 0 | 0 | 61 | 86 |
| 127. | 0 | 0 | 59 | 99 |
| 128. | 0 | 0 | 38 | 80 |
| 129. | 0 | 0 | 69 | 86 |
| 130. | 0 | 16 | 59 | 97 |
| 131. | 0 | 23 | 58 | 93 |
| 132. | 8 | 20 | 40 | 67 |
| 133. | 0 | 10 | 59 | 97 |
| 134. | — | — | 56 | 90 |
| 135. | 0 | 10 | 54 | 96 |
| 136. | — | — | 50 | 90 |
| 137. | — | — | 53 | 88 |
| 138. | — | — | 63 | 69 |
| 139. | — | — | 65 | 70 |
| 140. | — | — | 68 | 66 |
| 141. | — | — | 65 | 86 |
| 142. | — | — | 59 | 63 |
| 143. | — | — | 52 | 69 |
| 144. | — | — | 59 | 78 |
| 145. | 0 | 30 | 60 | 87 |

In practice, a pure compound can be used as an herbicide. However, in general, the compounds are first formulated with one or more inert carriers or diluents suitable for herbicidal use, before being applied.

The compositions or formulations, including a compound as described herein, may exist in any one of a number of solid or liquid forms. Examples of liquid forms are emulsifiable concentrates, flowables and pastes. Such compositions may contain, in addition to the active compound or compounds, various carriers or diluents; surface active agents (wetting agents, dispersing agents and/or emulsifying agents); solvents (water, or organic solvents such as aromatic solvents or chlorinated aliphatic solvents); adhesives; thickeners; binders; antifoaming agents; and other substances as mentioned herein. Solid carriers or diluents included in such compositions or formulations may include, for example, ground natural minerals such as kaolins, alumina, calcium carbonate, silica, kieselguhr, clay, etc.; ground synthetic minerals such as various silicates and aluminosilicates and ground vegetable products such as bark, cornmeal, sawdust, cellulose powder and the like.

To manufacture solid compositions, the active substances are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles. Pellets or granules can be manufactured by extrusion with appropriate carriers and binders.

Wettable powders, flowables, and pastes are obtained by mixing and grinding an active compound with one or more dispersing agents and/or solid carriers or diluents. Also included may be wetting agents and/or dispersing agents, for example, lignins, methyl cellulose, naphthalenesulfonic acid derivatives, fatty alcohol sulfates and various types of alkali and alkaline earth metal salts of fatty acids.

Emulsifiable concentrates are generally obtained by dissolving the active compound in an organic solvent, for example, butanol, cyclohexanone, xylenes, or higher boiling aromatic hydrocarbons. To obtain suspensions or emulsions in water, wetting agents are generally also added.

The compositions may also be used in the form of microcapsules. Microcapsules consist of fully enclosed or encapsulated droplets or granules containing the active compound, enclosed within an inert porous membrane, so as to permit escape of the encapsulated material into the surrounding medium or environment at a controlled rate.

Useful encapsulating materials include natural and synthetic rubbers or latexes, cellulosic materials, styrenebutadiene copolymers, polyacrylonitriles, polyacrylates, polyesters, polyamides, polyurethanes and starch xanthates.

It is possible to use highly concentrated liquid compositions containing up to about 95% by weight of the active compound, or even the active compound alone for those compounds which are liquids, when applying the compound in the form of a finely divided liquid by use of various atomizing equipment, for example by airplane crop-spraying techniques. For other purposes, however, the various types of compositions which can be utilized for these compounds will contain varying amounts of the compound according to the type of composition and the intended use.

In general, compositions may contain from 0.1 to 95% of the active compound, more preferably from 0.5 to 90%. Some typical compositions will contain an active compound as follows: Wettable powders, flowables and pastes - 20 to 90% active compound; oil suspensions, emulsions, solutions and emulsifiable concentrates - 5 to 90% active compound; aqueous suspensions - 10 to 50% active compound; dusts and powders - 1 to 25% active compound; granules and pellets - 1 to 20% active compound.

The rate of application of the active compound to a locus to be controlled will depend on the activity of the compound and/or composition and the nature of the seeds and plants to be controlled and will vary from about 0.05 to about 50 pounds per acre (about 0.06 to about 56 kg/ha).

Compositions containing one or more of the active compounds described, in a herbicidally effective amount, may be applied to the plant or locus to be controlled in any conventional manner. Thus, powders and various liquid compositions containing the active compound can be applied by the use of power dusters, boom and hand sprayers and spray spray dusters, or applied from airplanes as mists or sprays. When applied in the latter method, they may be effective in very low dosages. To modify or control growth of germinating seeds or emerging seedlings, liquid compositions may be applied to the soil with conventional methods and may be distributed in the soil to a depth of one-half inch below the soil surface. The compositions need not be admixed with the soil particles, but can be applied merely by sprinkling on the surface of the soil.

Compositions including active compounds may also be applied by addition to irrigation waters supplied to the field to be treated. This method of application permits penetration of the compounds into the soil as the water is absorbed therein.

| EXAMPLES OF TYPICAL COMPOSITIONS | |
|---|---|
| | Oil |
| Ingredient | Weight % |

EXAMPLES OF TYPICAL COMPOSITIONS

| | |
|---|---|
| Active Compound | 1 |
| Oil solvent-heavy aromatic naphtha | 99 |
| Total | 100 |

Emulsifiable Concentrate

| | |
|---|---|
| Active Compound | 50 |
| Kerosene | 45 |
| Emulsifying agent (mixture of long chain ethoxylated polyethers with long chain sulfonate) | 5 |
| Total | 100 |

Emulsifiable Concentrate

| | |
|---|---|
| Active Compound | 90 |
| Kerosene | 5 |
| Emulsifying agent (mixture of long chain ethoxylated polyethers with long chain sulfonate) | 5 |
| Total | 100 |

Dusts and/or Powders

| Ingredient | Wt. % | Wt. % | Wt. % |
|---|---|---|---|
| Active Compound | 0.5 | 50.0 | 90.0 |
| Attapulgite Clay Powder | 93.5 | 44.0 | 4.0 |
| Sodium lignin sulfonate | 5.0 | 5.0 | 5.0 |
| Sodium dioctyl sulfosuccinate | 1.0 | 1.0 | 1.0 |
| TOTAL | 100.0 | 100.0 | 100.0 |

The compositions of the invention may comprise, in addition to one or more compounds of the invention, one or more compounds not of the invention but which possess biological activity. Compounds not of this invention may be other pesticidal agents, such as herbicides, fungicides, insecticides, acaricides, nematocides, bactericides, and plant growth regulators. Such compositions may also contain soil disinfectants or fumigants and may further contain fertilizers, thus making it possible to provide multi-purpose compositions containing one or more of the compounds described herein as well as, optionally, other pesticides and also fertilizers, all intended and formulated for use at the same locus. Accordingly, in yet a still further embodiment, the invention provides an herbicidal composition comprising a mixture of at least one herbicidal compound of formula (I) as hereinbefore defined with at least one other herbicide.

The other herbicide may be any herbicide not having the formula (I). It will generally be an herbicide having a complementary action in the particular application.

Examples of useful complementary herbicides include:

A. Benzo-2,1,3-thiodiazin-4-one-2,2-dioxides such as 3-isopropylbenzo-2,1,3-thiadiazin-4-one-2,2-dioxide (bentazone);

B. hormone herbicides, particularly the phenoxy alkanoic acids such as 4-chloro-2-methylphenoxy acetic acid (MCPA), S-ethyl 4-chloro-O-tolyloxy thio-acetate (MCPA-thioethyl), 2-(2,4-dichlorophenoxy) propionic acid (dichlorprop), 2,4,5-trichlorophenoxyacetic acid (2,4,5-T), 4-(4-chloro-2-methylphenoxy)butyric acid (MCPB), 2,4-dichlorophenoxyacetic acid (2,4-D), 4-(2,4-dichlorophenoxy)butyric acid (2,4-DB), 2-(4-chloro-2-methylphenoxy) propionic acid (mecoprop), 3,5,6-trichloro-2-pyridyloxyacetic acid (trichlopyr), 4-amino-3,5-dichloro-6-fluoro-2-pyridyloxyacetic acid (fluroxypyr), 3,6-dichloropyridine-2-carboxylic acid (clopyralid), and their derivatives (e.g. salts, esters and amides);

C. 1,3-dimethylpyrazole derivatives such as 2-[4-(2,4-dichlorobenzoyl) 1,3-dimethylpyrazol-5-yloxy] acetophenone (pyrazoxyfen), 4-(2,4-dichlorobenzoyl)1,3-dimethylpyrazol-5-yltoluene sulfonate (pyrazolate) and 2-[4-(2,4-dichloro-m-toluolyl)-1,3-dimethylpyrazol-5-yloxy]4'-methylacetophenone (benzofenap);

D. Dinitrophenols and their derivatives (e.g. acetates such as 2-methyl-4,6-dinitrophenol (DNOC), 2-t-butyl-4,6-dinitrophenol (dinoterb), 2-sec.-butyl-4,6-dinitrophenol (dinoseb) and its ester, dinoseb acetate;

E. dinitroaniline herbicides such as N',N'-diethyl-2,6-dinitro-4-trifluoromethyl-m-phenylenediamine (dinitramine), 2,6-dinitro-N,N-dipropyl-4-trifluoromethylaniline (trifluralin), N-ethyl-N-(2-methylallyl)-2,6-dinitro-4-trifluoromethylaniline (ethalfluralin), N-(1-ethylpropyl)- 2,6-dinitro-3,4-xylidine (pendimethalin); and 3,5-dinitro-$N^4$, $N^4$-dipropylsulphanilamide (oryzalin);

F. arylurea herbicides such as N'-(3,4-dichlorophenyl)-N,N-dimethylurea (diuron), N,N-dimethyl-N'-[3-(trifluoromethyl) phenyl]urea (flumeturon), 3-(3-chloro-4-methoxyphenyl)-1,1-dimethylurea(metoxuron), 1-butyl-3-(3,4-dichlorophenyl)-1-methylurea(neburon), 3-(4-isopropylphenyl)-1,1-dimethylurea (isoproturon), 3-(3-chloro-p-tolyl)-1,1-dimethylurea(chlorotoluron), 3-[4-(4-chlorophenoxy) phenyl]-1,1-dimethylurea (chloroxuron), 3-(3,4-dichlorophenyl)-1-methylurea (linuron), 3-(4-chlorophenyl)-1-methoxy-1-methylurea (monolinuron), 3-(4-bromo-4-chlorophenyl)-1-methoxy-1-methylurea (chlorobromuron), 1-(1-methyl-1-phenylethyl)-3-p-tolylurea(daimuron), and 1-benzothiazol-2-yl-1,3-dimethylurea (methabenzthiazuron);

G. phenylcarbamoyloxyphenylcarbamates such as 3-[methoxycarbonylamino]phenyl (3-methylphenyl)-carbamate (phenmedipham) and 3-[ethoxycarbonylamino]-phenyl phenylcarbamate (desmedipham);

H. 2-phenylpyridazin-3-ones such as 5-amino-4-chloro-2-phenylpyridazin-3-one (chloridazon), and 4-chloro-5-methylamino-2-($\alpha,\alpha,\alpha$-trifluoro- m-tolyl) pyridazin-3(2H)-one (norflurazon);

I. uracil herbicides such as 3-cyclohexyl-5,6-trimethyleneuracil (lenacil), 5-bromo-3-sec.-butyl-6-methyluracil (bromacil) and 3-t-butyl-5-chloro-6-methyl-uracil (terbacil);

J. triazine herbicides such as 2-chloro-4-ethylamino-6-(i-propylamino)-1,3,5-triazine (atrazine), 2-chloro-4,6-di(ethylamino)-1,3,5-triazine (simazine), 2-azido-4-(i-propylamino)-6-methylthio-1,3,5- triazine (aziprotryne), 2-(4-chloro-6-ethylamino-1,3,5-triazin-2-ylamino)-2-methylpropionitrile (cyanazine), $N^2$, $N^4$-diisopropyl-6-methylthio-1,3,5-triazine-2,4-diamine (prometryn), $N^2$-(1,2-dimethylpropyl)-$N^4$-ethyl-6-methylthio-1,3,5-triazine-2,4 -diamine (dimethametryn), $N^2,N^4$-diethyl-6-methylthio-1,3,5-triazine-2,4-diamine (simetryne), and $N^2$-tert.-butyl-$N^4$-ethyl-6-methylthio-1,3,5-triazine-2,4-diamine (terbutryn);

K. phosphorothioate herbicides such as S-2-methyl-piperidinocarbonyl-methyl O,O-dipropyl phosphorodithioate (piperophos), S-2-benzenesulphonamidoethyl O,O-diisopropyl phosphonodithioate (bensulide), and O-ethyl O-6-nitrom-tolyl sec.-butylphosphoamidothioate (butamifos);

L. thiolcarbamate herbicides such as S-ethyl N-cyclohexyl-N-ethyl thiocarbamate (cycloate), S-propyl dipropyl-thiocarbamate (vernolate), S-ethyl-azepine-1-carbothioate (molinate), S-4-chlorobenzyl diethylthiocarbamate (thiobencarb), S-ethyl di-isobutyl- thiocarbamate (butylate)*, S-ethyl di-isopropylthiocarbamate (EPTC)*, S-2,3,3-trichloroallyl di-isopropyl thiocarbamate (tri-allate), S-2, 3-di-chloroallyl di-isopropyl thiocarbamate (di-allate), S-benzyl 1,2-dimethylpropyl (ethyl) thiocarbamate (esprocarb), S-benzyl di(sec.-butyl) thiocarbamate (tiocarbazil), 6-chloro-3-phenyl-pyridazin 4-yl S-octyl thiocarbamate (pyridate), and S-1-methyl-1-phenylethylpiperidine-1-carbothioate (dimepiperate);

* These compounds are preferably employed in combination with a safener such as 2,2-dichloro-N,N-di-2-propenylacetamide (dichlormid).

M. 1,2,4-triazin-5-one herbicides such as 4-amino-4,5-dihydro-3-methyl-6-phenyl-1,2,4-triazine-5-one(-metamitron) and 4-amino-6-butyl-4,5-dihydro-3-methylthio-1,3,4-triazin-5-one (metribuzin);

N. benzoic acid herbicides such as 2,3,6-trichlorobenzoic acid (2,3,6-TBA), 3,6-dichloro-2-methoxybenzoic acid (dicamba) and 3-amino-2, 5-dichloro benzoic acid (chloramben);

O. anilide herbicides such as 2-chloro-2',6'-diethyl-N-(2-propoxyethyl)acetanilide (pretilachlor), N-butoxymethyl-chloro-2',6'-diethylacetanilide (butachlor), the corresponding N-methoxy compound (alachlor), the corresponding N-i-propyl compound (propachlor), 3',4'- dichloropropionilide (propanil), 2-chloro-N-[pyrazol-1- ylmethyl]acet-2'-6'xylidide(metazachlor), 2-chloro-6'-ethyl- N-(2-methoxy-1-methylethyl) acet-O-toluidide (metolachlor), 2-chloro-N-ethoxymethyl-6'-ethylacet-O-toluidide (acetochlor), and 2-chloro-N-(2-methoxyethyl)acet-2',6'-xylidide (dimethachlor);

P. dihalobenzonitrile herbicides such as 2,6-dichlorobenzonitrile (dichlobenil), 3,5-dibromo-4-hydroxybenzonitrile (bromoxynil) and 3,5-diiodo-4-hydroxy-benzonitrile (ioxynil);

Q. haloalkanoic herbicides such as 2,2-dichloropropionic acid (dalapon), trichloroacetic acid (TCA) and salts thereof;

R. diphenylether herbicides such as ethyl 2-[5-(2-chloro-trifluoro-p-tolyloxy)-2- nitrobenzoylooxy propionate (lactofen), D-[5-(2-chloro-α,α,α-trifuoro-p-tolyl)-2-nitrobenzoyl] gycolic acid (fluroglycofen) or salts or ester thereof, 2,4-dichlorophenyl-4- nitrophenyl ether (nitrofen), methyl-(2,4- dichlorophenoxy)-2-nitrobenzoate (bifenox), 2-nitro-5-(2-chloro-4-trifluoromethylphenoxy) benzoic acid (aciflurofen) and salts and esters thereof, 2-chloro-4-trifluoromethylphenyl 3-ethoxy-4-nitrophenyl ether (oxyfluorfen) and 5-(2-chloro-4-(trifluoromethyl) phenoxy)-N-(methylsulfonyl)-2-nitrobenzamide (fomesafen); 2,4,6-trichlorophenyl 4-nitrophenyl ether (chlornitrofen) and 5-(2,4-dichlorophenoxy)-2-nitroanisole (chlomethoxyfen);

S. phenoxyphenoxypropionate herbicides such as (RS)-2-[4-(2,4-dichloro-phenoxy)phenoxy) propionic acid (diclofop) and esters thereof such as the methyl ester, 2-(4-(5-trifluoromethyl)-2-(pyridinyl)oxy) penoxypropanoic acid (fluazifop) and esters thereof, 2-(4-(3-chloro-5-trifluoro-methyl)-2-pyridinyl)oxy)phenoxy) propanoic acid (haloxyfop) and esters thereof, 2-(4-((6-chloro-2-quinoxalinyl)oxy) phenoxypropanoic acid (quizalofop) and esters thereof and (±)-2-[4-(6-chlorobenzoxazol-2-yloxy)-phenoxy]propionic acid (fenoxaprop) and esters thereof such as the ethyl ester;

T. cyclohexanedione herbicides such as 2,2-dimethyl-4,6-dioxo-5-(1-((2-propenyloxy)-imino)-butyl) cyclohexane carboxylic acid (alloxydim) and salts thereof, 2-(1-ethoxyimino) butyl-5-(2-(ethylthio)-propyl)-3-hydroxy-2-cyclohexan-1- one(sethoxydim), 2-(1-ethoxyimino) butyl)-3-hydroxy-5-thian-3-ylcyclohex-2-enone (cyclyoxydim)2-[1(ethoxyimino)propyl]-3-hydroxy-5-mesitylcyclohex-2-enone(tralkoxydim), and (±)-2-((E)-1-[(E)-3-chloroallyloximino] propyl)-5-[2-(ethylthio)-propyl]-3-hydroxycyclohex-2-enone (clethodim);

U. sulfonyl urea herbicides such as 2-chloro-N (4-methoxy-6-methyl-1,3,5-triazin-2-yl)-aminocarbonyl) benzenesulphonamide (chlorosulfuron), methyl 2-((((4,6-dimethyl2-pyrimidinyl)amino)-carbonyl)amino)-sulphonylbenzoic acid sulfometuron), 2-(((3-(4-methoxy-6-methyl-1,3,5-triazin-2-yl)carbonyl) amino)-sulphonyl)benzoic acid (metsulfuron) and esters thereof; -(4,6-dimethoxypyrimidin-2-ylcarbamoylsuphamoy)-O-toluic acid (benzsulfuron) and esters thereof such as the methyl3-[3-(4-methoxy-6methyl-1,3,5-triazin-2-yl)ureidosulphonyl]thiophene-2-carboxylate(DPX-M6313), 2-(4-chloro-6-methoxy pyrimidin-2-yl carbamoylsulphamoyl benzoic acid (chlorimuron) and esters such as the ethyl ester thereof 2-(4,6-dimethoxypyrimidin-2-ylcarbamoylsulphamoyl)-N, N-dimethyl-nicotinamide, 2-[4,6-bis(difluoromethoxy)-pyrimidin2-ylcarbamoylsulphamoyl) benzoic acid (pirimisulfuron) and esters such as the methyl ester thereof, 2-[3-(4-methoxy-6-methyl-1,3,5-triazin-zyl)-3-methylureidosulphonyl) benzoic acid esters such as the methyl ester thereof (DPX-LS300) and 5-(4,6-dimethoxypyrimidin-2-ylcarbamoylsulphamoyl)-1-methyl-pyrazole-4- carboxylic acid (pyrazosulfuron);

V. imidazolidinone herbicides such as 2-(4,5-dihydro-4-isopropyl-4-methyl-5-oxoimidazol-2- yl) quinoline-3-carboxylic acid (imazaquin), methyl 6-(4-isopropyl-4-methyl-5-oxo-2-imidazolin-2-yl)-m-toluate and p-toluate isomer(imazamethabenz),2-(4-isopropyl-4-methyl-5-oxo-2-imidazolin-2-yl) nicotinic acid (imazapyr) and isopropylammonium salts thereof, (RS)-5-ethyl-2-(4-isopropyl-4-methyl-5-oxo-2-imidazolin-2-yl) nicotinic acid (imazethapyr);

W. arylanilide herbicides such as benzoyl-N-(3-chloro-4-fluorophenyl)-L-alanine (flamprop) and esters thereof, ethyl N-benzoyl-N-(3,4-dichlorophenyl)-DL-alaninate (benzoylprop -ethyl), N-(2,4-difluorophenyl)-2-(3-trifluoromethyl)phenoxy)-3- pyridinecarboxamide (diflufenican);

X. amino acid herbicides such as N-(phosphonomethyl)-glycine (glyphosate) and DL-homoalanin-4-yl (methyl)phosphinic acid (gluyfosinate) and their salts and esters, trimethylsulfonium N-(phosphonomethyl)-glycine (sulphosate), and bilanafos;

Y. organoarsenical herbicides such as monosodium methanearsonate (MSMA);

Z. herbicidal amide derivative such as (RS)N,N-diethyl-2-(1-naphthyloxypropionamide) (napropamide), 3,5-dichloro-N-(1,1- dimethylpropynyl)benzamide (propyzamide), (R)-1-(ethylcarbamoyl)ethyl carbanilate (carbetamide), N-benzyl-N-isopropylpivalamide (tebutam), (RS)-2-bromo-N-(α,α-dimethylbenzyl)-3,3-dimethylbutyramide (bromobutide), N-[3-(1-ethyl-1-methylpropyl)-isoxazol-5-yl] 2,6-dimethoxybenzamide, (isoxaben), N-phenyl-2-(2-naphthyloxy) propionamide (naproanilide), N,N-dimethyl-diphenylacetamide (diphenamid), and N-(1-naphthyl)-phthalamic acid (naptalam);

AA. miscellaneous herbicides including 2-ethoxy-2,3-dihydro-3, 3-dimethylbenzofuran methanesulfonate (ethofumesate), 7-oxabicyclo (2.2.1)heptane,1-methyl-4-(1-methylethyl)-2-(2-methylphenylmethoxy)-exo (cinmethylin), 1,2-dimethyl-3,5-diphenylpyrazolium ion (difenzoquat) and salts thereof such as the methyl sulfate salt, 2-(2-chlorobenzyl)-4,4- dimethyl-1,2-oxazoldin-3-one (clomazone), 5-tert.-butyl-3-(2,4-dichloro-5-isopropoxyphenyl)-1,3,4- oxadiazol2(3H)-one (oxadiazon), 3,5-dibromo-4-hydroxy benzaldehyde 2,4-dinitrophenyloxime (bromofenoxim), 4-chlorobut-2-ynyl-3-chlorocarbanilate (barban), (RS)-2-(3,5-dichlorophenyl)-2-(2,2,2-trichloroethyl)oxirane (tridiphane), (3RS,4RS; 3RS,4SR)-3-chloro-4-chloromethyl-1-α,α-trifluro-m-totyl(-2-pyrrolidone (in the ratio 3:1) flurochloridone), dichloroquinoline 8-carboxylic acid (quinchlorac) and 2-(1,3-benzothiazol-2-yl-oxy)-N-methylacetanilide (mefanacet);

BB. examples of useful contact herbicides include bipyridylium herbicides such as those in which the active entity is the 1,1'-dimethyl-4,4'-dipyridylium ion (paraquat) and those in which the active entity is the 1,1'-ethylene-2,2'-dipyridylium ion (diquat).

What is claimed is:

1. A compound having the formula

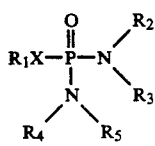

in which X is sulfur; $R_1$ is $C_1$–$C_6$ alkyl, phenyl, tolyl, chlorophenyl or 3,4-dichlorophenyl; $R_2$ is $C_1$–$C_4$ alkyl; $R_3$ is pyridyl, phenyl or substituted phenyl in which the substituents are halogen, $C_1$–$C_4$ alkyl, $C_1$–$C_4$ alkoxy, $C_1$–$C_4$ haloalkoxy, nitro and/or cyano; or $R_2$ and $R_3$ taken together form an alkylene chain having from 2 to 6 carbon atoms optionally substituted by up to two $C_1$–$C_4$ alkyl groups; $R_4$ and $R_5$ are each $C_2$–$C_6$ alkyl; or $R_3$ and $R_5$ taken together form an alkylene chain having from 2 to 5 carbon atoms;

provided that $R_3$ is not 2,3,6-trifluorophenyl.

2. A compound according to claim 1 in which X is sulfur.

3. A compound according to claim 2 in which $R_1$ is alkyl.

4. A compound according to claim 3 in which $R_3$ is phenyl or substituted phenyl.

5. A compound according to claim 4 in which $R_2$ is methyl.

6. A compound according to claim 5 in which $R_4$ and $R_5$ are identical $C_1$–$C_4$ alkyl groups.

7. A compound according to claim 3 in which $R_3$ is pyridyl.

8. A compound according to claim 3 in which $R_2$ and $R_3$ taken together form an alkylene chain, optionally substituted.

9. A compound according to claim 1 in which $R_3$ is phenyl substituted by up to 4 fluorine atoms, and optionally further substituted with a methyl group.

10. A compound according to claim 1 in which X is sulfur, $R_1$ is n-propyl, $R_2$ is methyl, $R_3$ is 2,4-difluorophenyl and $R_4$ and $R_5$ are both n-propyl.

11. A compound according to claim 1 in which X is sulfur, $R_1$ is n-propyl, $R_2$ is methyl, $R_3$ is 3,4-difluorophenyl and $R_4$ and $R_5$ are both n-propyl.

12. A compound according to claim 1 in which X is sulfur, $R_1$ is n-propyl, $R_2$ is methyl, $R_3$ is 4-methoxyphenyl and $R_4$ and $R_5$ are both n-propyl.

13. A compound according to claim 1 in which X is sulfur, $R_1$ is n-propyl, $R_2$ is methyl, $R_3$ is 2,4,5-trifluorophenyl and $R_4$ and $R_5$ are both n-propyl.

14. A compound according to claim 1 in which X is sulfur, $R_1$ is n-propyl, $R_2$ is methyl, $R_3$ is 2,3,5,6-tetrafluorophenyl and $R_4$ and $R_5$ are both n-propyl.

15. A compound according to claim 1 in which X is sulfur, $R_1$ is n-propyl, $R_2$ is ethyl, $R_3$ is 4-fluorophenyl and $R_4$ and $R_5$ are both n-propyl.

16. A compound according to claim 1 in which X is sulfur, $R_1$ is n-propyl, $R_2$ is n-butyl, $R_3$ is 4-fluorophenyl and $R_4$ and $R_5$ are both n-propyl.

17. A compound according to claim 1 in which X is sulfur, $R_1$ is n-propyl, $R_2$ is methyl, $R_3$ is 2-isopropylphenyl and $R_4$ and $R_5$ are both n-propyl.

18. A compound according to claim 1 in which X is sulfur, $R_1$ is n-propyl, $R_2$ is n-propyl, $R_3$ is 2-isopropylphenyl and $R_4$ and $R_5$ are both n-propyl.

19. A compound according to claim 1 in which X is sulfur, $R_1$ is n-propyl, $R_2$ is methyl, $R_3$ is 2-methyl,4-fluorophenyl and $R_4$ and $R_5$ are both n-propyl.

20. A compound according to claim 1 in which X is sulfur, $R_1$ is n-propyl, $R_2$ is methyl, $R_3$ is 2-methyl,5-fluorophenyl and $R_4$ and $R_5$ are both n-propyl.

21. A compound according to claim 1 in which X is sulfur, $R_1$ is n-propyl, $R_2$ and $R_3$ taken together are 1-methyl, 4-ethylpentamethylene, and $R_4$ and $R_5$ are both n-propyl.

22. A compound according to claim 1 in which X is sulfur, $R_1$ is n-propyl, $R_2$ is methyl, $R_3$ is 2-pyridyl; and $R_4$ and $R_5$ are both n-pentyl.

* * * * *